(12) United States Patent
Katsuyama (10) Patent No.: US 11,051,789 B2
(45) Date of Patent: Jul. 6, 2021

(54) ULTRASOUND IMAGE DIAGNOSTIC APPARATUS

(71) Applicant: FUJIFILM Corporation, Tokyo (JP)

(72) Inventor: Kimito Katsuyama, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 433 days.

(21) Appl. No.: 14/551,812

(22) Filed: Nov. 24, 2014

(65) Prior Publication Data

US 2015/0080734 A1 Mar. 19, 2015

Related U.S. Application Data

(63) Continuation of application No. PCT/JP2013/064038, filed on May 21, 2013.

(30) Foreign Application Priority Data

May 25, 2012 (JP) .............................. JP2012-120011

(51) Int. Cl.
*A61B 8/08* (2006.01)
*A61B 8/00* (2006.01)
*A61B 8/14* (2006.01)

(52) U.S. Cl.
CPC .............. *A61B 8/5215* (2013.01); *A61B 8/14* (2013.01); *A61B 8/4488* (2013.01); *A61B 8/463* (2013.01); *A61B 8/469* (2013.01); *A61B 8/5269* (2013.01)

(58) Field of Classification Search
CPC ......... A61B 8/00; A61B 8/5215; A61B 8/463; A61B 8/5269; A61B 8/4488; A61B 8/14; A61B 8/469
See application file for complete search history.

(56) References Cited

U.S. PATENT DOCUMENTS 5,588,435 A * 12/1996 Weng .................. A61B 8/0866
600/443
6,099,473 A * 8/2000 Liu ....................... A22B 5/007
382/110

(Continued)

FOREIGN PATENT DOCUMENTS

JP 4-44906 U 4/1992
JP 2007-330286 A 12/2007

(Continued)

OTHER PUBLICATIONS

International Preliminary Report on Patentability dated Dec. 4, 2014 (Forms PCT/IB/338, PCT/IB/373 and PCT/ISA/237.

(Continued)

*Primary Examiner* — Sean D Mattson
(74) *Attorney, Agent, or Firm* — Birch, Stewart, Kolasch & Birch, LLP (57) ABSTRACT

The present invention aims at providing an ultrasound image diagnostic apparatus capable of shortening the time required for measurement and calculation of an optimal sound velocity and obtaining an ultrasound image having excellent image quality at a tissue or lesion the operator desires to observe. There are provided an element data memory storing element data; a region-of-interest setter setting a region of interest; an optimal sound velocity calculator calculating an optimal sound velocity at the region of interest using the element data corresponding to the region of interest; a reconstruction region setter setting a reconstruction region that contains the region of interest and is larger than the region of interest; and an image reconstructor generating a reconstructed image by reconstructing the ultrasound image in the reconstruction region based on the optimal sound velocity.

5 Claims, 3 Drawing Sheets

(56) References Cited

U.S. PATENT DOCUMENTS

| | | | | | |
|---|---|---|---|---|---|
| 6,123,670 | A | * | 9/2000 | Mo | A61B 8/469 600/447 |
| 6,193,660 | B1 | * | 2/2001 | Jackson | A61B 8/00 600/443 |
| 6,368,279 | B1 | * | 4/2002 | Liu | A61B 8/00 600/443 |
| 8,002,705 | B1 | * | 8/2011 | Napolitano | G01S 7/52019 600/407 |
| 2003/0171668 | A1 | * | 9/2003 | Tsujino | A61B 8/0883 600/407 |
| 2003/0212327 | A1 | * | 11/2003 | Wang | A61B 6/463 600/437 |
| 2007/0167784 | A1 | * | 7/2007 | Shekhar | A61B 6/032 600/443 |
| 2010/0076312 | A1 | * | 3/2010 | Katsuyama | A61B 8/00 600/443 |
| 2011/0082372 | A1 | * | 4/2011 | Tateyama | A61B 8/0833 600/443 |

FOREIGN PATENT DOCUMENTS

| | | |
|---|---|---|
| JP | 2011-229817 A | 11/2011 |
| JP | 2012-45198 A | 3/2012 |

OTHER PUBLICATIONS

International Search Report, issued in PCT/JP2013/064038, dated Aug. 27, 2013.
International Search Report, issued in PCT/JP2013/084038, dated Aug. 27, 2013.

* cited by examiner

ULTRASOUND IMAGE DIAGNOSTIC APPARATUS

CROSS REFERENCE TO RELATE APPLICATIONS

This application is a continuation application of International Application No. PCT/JP2013/064038 filed on May 21, 2013, which claims priority under 35 U.S.C. 119(a) to patent application Ser. No. 2012-120011 filed in Japan on May 25, 2012, all of which are hereby expressly incorporated by reference into the present application.

BACKGROUND OF THE INVENTION

The present invention relates to an ultrasound image diagnostic apparatus that generates an ultrasound diagnostic image for use in diagnosis by imaging an organ and the like in a living body through transmission and reception of ultrasonic waves.

Conventionally, ultrasound diagnostic apparatuses that use ultrasound images have been put to practical use in the medical field. In general, this type of ultrasound diagnostic apparatus comprises an ultrasound probe having a built-in transducer array and an apparatus body connected to the ultrasound probe. The ultrasound probe transmits ultrasonic waves toward a subject and receives ultrasonic echoes from the subject, and the apparatus body electrically processes the reception signals to generate an ultrasound image.

When such an ultrasound diagnostic apparatus generates an ultrasound image, the sound velocity in a living body of a subject is assumed to be constant. However, in an actual living body, the sound velocity varies depending on the nature of an organ in the living body and thus there is variability among sound velocities. The variability causes deterioration in image quality of an ultrasound image, such as spatial distortion and decrease in contrast or spatial resolution.

In recent years, in order to more accurately diagnose a diagnosis site in a subject, a sound velocity value at a given diagnosis site is optimized to minimize distortion of an image, decrease in spatial resolution and the like to thereby improve the image quality.

For instance, JP 2011-229817 A describes having evaluation means that calculates an evaluation value indicative of a degree of variability of phase information based on plural pieces of phase information obtained with respect to all or a part of plural reception signals after delay processing but before addition processing; and determination means that determines an optimal value of a sound speed parameter value based on the change in the evaluation value occurring with varying sound speed parameter value, thereby obtaining the optimal sound speed value, wherein an ultrasound image is generated using the optimal sound speed value to thereby improve spatial resolution of the resulting ultrasound image. Furthermore, JP 2011-229817 A describes that the optimal sound speed value at a region of interest (ROI) set by the operator is obtained based on the degree of variability of phase information among the plural reception signals after delay processing but before addition processing.

Owing to the configuration in which a region of interest is set in an ultrasound image and the optimal sound speed value at the region of interest is obtained, it is possible to prevent distortion of the image from occurring in the region of interest, i.e., at a tissue or lesion the operator desires to observe, and improve spatial resolution of the image, while the optimal sound speed value, which is generally obtained through time-consuming calculation, can be obtained in a short time, thus shortening the time required for calculation.

SUMMARY OF THE INVENTION

However, in the case where a region of interest is set in an ultrasound image, a tissue or lesion the operator desires to observe may be displaced from the set region of interest due to movement of the probe or tissue. When a region of interest is set and the optimal sound speed value at the region of interest is obtained to thereby generate an ultrasound image, the ultrasound image is generated with the sound speed value optimal for a tissue or lesion the operator desired to observe in the region of interest, whereas the ultrasound image is generated with a sound speed value different from the sound speed value optimal for the tissue or lesion the operator desires to observe in a region other than the region of interest. Accordingly, when the tissue or lesion the operator desires to observe is displaced from the region of interest, this may adversely affect the image quality.

The present invention aims at solving the foregoing problems of the prior art and providing an ultrasound image diagnostic apparatus capable of shortening the time required for measurement and calculation of an optimal sound velocity and obtaining an ultrasound image having excellent image quality at a tissue or lesion the operator desires to observe.

In order to attain the above objects, the present invention provides an ultrasound image diagnostic apparatus, comprising: a transducer array having a plurality of oscillators and adapted to transmit an ultrasonic wave toward a subject, receive an ultrasonic echo from the subject and output element data which is a reception signal of each of the plurality of oscillators; an image generator adapted to generate an ultrasound image based on a sound ray signal produced from the element data output by the transducer array; an element data memory adapted to store the element data that each of the plurality of oscillators of the transducer array has output upon receipt of an ultrasonic echo; a region-of-interest setter adapted to set a region of interest in the ultrasound image generated by the image generator; a region-of-interest element data acquirer adapted to acquire element data corresponding to the region of interest; an optimal sound velocity calculator adapted to calculate an optimal sound velocity at the region of interest using the element data corresponding to the region of interest as acquired; a reconstruction region setter adapted to set a reconstruction region that contains the region of interest and is larger than the region of interest; and an image reconstructor adapted to generate a reconstructed image by reconstructing the ultrasound image in the reconstruction region using the element data stored in the element data memory based on the calculated optimal sound velocity.

Preferably, the reconstruction region setter sets the reconstruction region by adding a margin region having a preset width to the region of interest set by the region-of-interest setter.

It is preferable to include an image regenerator adapted to regenerate an ultrasound image using the ultrasound image generated by the image generator and the reconstructed image generated by the image reconstructor.

Preferably, the image regenerator regenerates an ultrasound image by replacing the reconstruction region of the ultrasound image by the reconstructed image.

Alternatively, the image regenerator preferably regenerates an ultrasound image by replacing the reconstruction region of the ultrasound image by an image obtained by synthesizing the ultrasound image in the reconstruction region and the reconstructed image.

Alternatively, the image regenerator preferably regenerates an ultrasound image by replacing the region of interest of the ultrasound image by the reconstructed image in the region of interest and replacing a margin region of the ultrasound image by an image obtained by synthesizing the ultrasound image in the margin region and the reconstructed image in the margin region at a ratio varied such that a proportion of the ultrasound image increases with increasing distance from the region of interest.

Preferably, the region-of-interest element data acquirer acquires the element data corresponding to the region of interest from the element data stored in the element data memory.

Alternatively, the region-of-interest element data acquirer preferably acquires element data that the transducer array has output upon transmission of an ultrasonic wave toward the region of interest and receipt of an ultrasonic echo.

Preferably, the region-of-interest setter sets the region of interest in accordance with an instruction input from an input device.

Alternatively, the region-of-interest setter preferably extracts a structural region based on a difference in brightness between adjacent pixels of the ultrasound image and sets a region containing the structural region as the region of interest.

According to the ultrasound image diagnostic apparatus of the invention having the foregoing configuration, it is possible to shorten the time required for measurement and calculation of an optimal sound velocity and obtain an ultrasound image having excellent image quality at a tissue or lesion the operator desires to observe.

DETAILED DESCRIPTION OF THE INVENTION

An ultrasound image diagnostic apparatus of the invention is described in detail below with reference to a preferred embodiment shown in the accompanying drawings.

Figure 1:
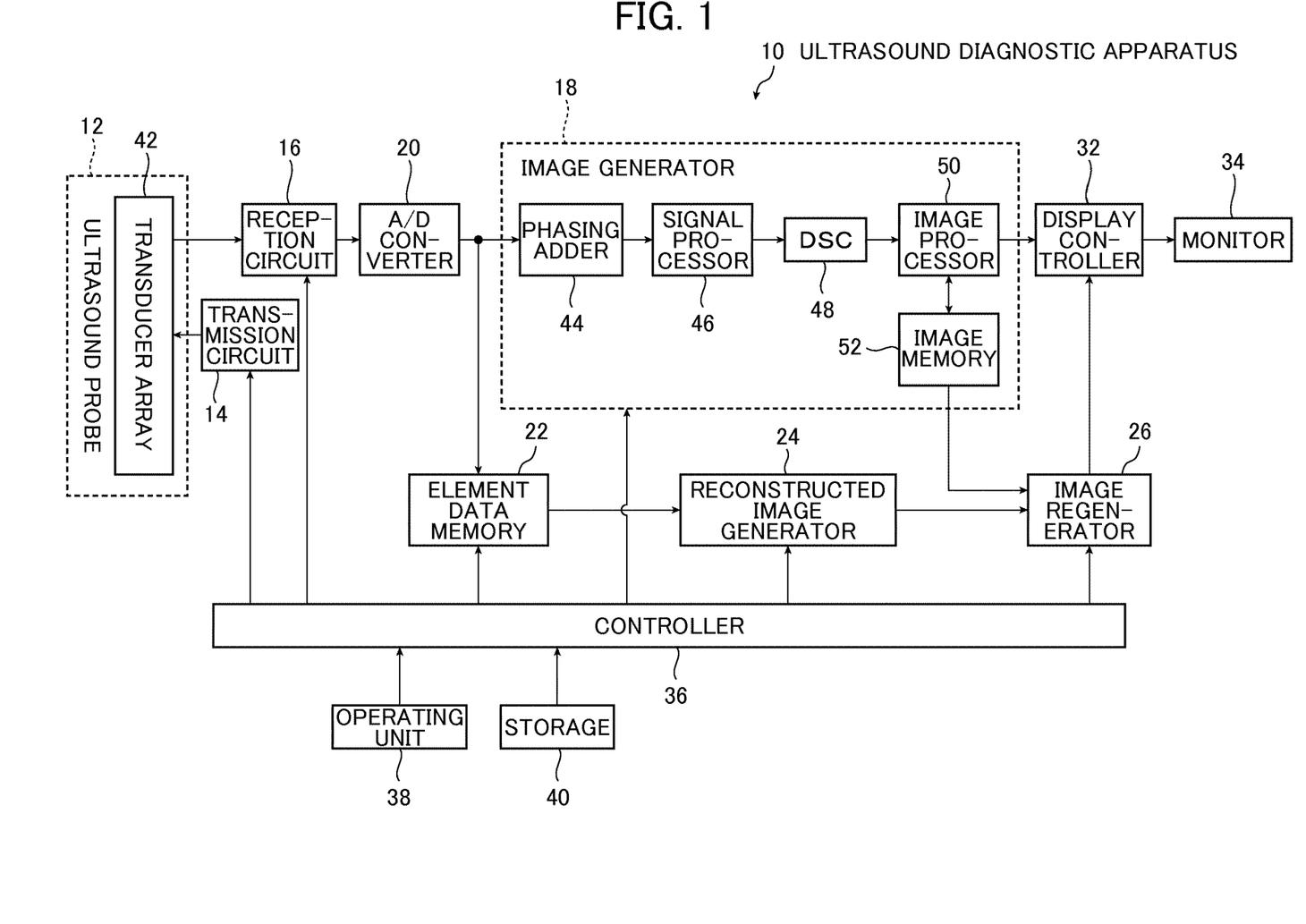
FIG. 1 is a block diagram conceptually showing the configuration of an ultrasound image diagnostic apparatus according to the present invention.

FIG. 1 is a block diagram conceptually showing an example of the configuration of the ultrasound image diagnostic apparatus (hereinafter also referred to as "ultrasound diagnostic apparatus") of the invention.

An ultrasound diagnostic apparatus 10 includes an ultrasound probe 12, a transmission circuit 14 and reception circuit 16 connected to the ultrasound probe 12, an A/D converter 20, an image generator 18, an element data memory 22, a reconstructed image generator 24, an image regenerator 26, a display controller 32, a monitor 34, a controller 36, an operating unit 38 and a storage 40.

The ultrasound probe 12 includes a transducer array 42 of type used in general ultrasound diagnostic apparatuses.

The transducer array 42 comprises a plurality of ultrasound transducers arranged one-dimensionally or two-dimensionally. During the generation of an ultrasound image, these ultrasound transducers transmit an ultrasonic beam according to driving signals supplied from the transmission circuit 14 to them, respectively, and receive an ultrasonic echo from the subject to output reception signals.

Each of the ultrasound transducers comprises an oscillator (element) composed of a piezoelectric body and electrodes each provided on either end of the piezoelectric body. The piezoelectric body is composed of, for example, a piezoelectric ceramic represented by a PZT (lead zirconate titanate), a piezoelectric polymer represented by PVDF (polyvinylidene fluoride), or a piezoelectric monocrystal represented by PMN-PT (lead magnesium niobate-lead titanate solid solution).

When a pulsed voltage or a continuous-wave voltage is applied across the electrodes of each oscillator, the piezoelectric body expands and contracts and the oscillator produces a pulsed or continuous ultrasonic wave. The thus produced ultrasonic waves are combined to form an ultrasonic beam. Upon reception of a propagating ultrasonic wave, each oscillator expands and contracts to produce an electric signal, which is in turn output as a reception signal of the ultrasonic wave.

The transmission circuit 14 including, for example, a plurality of pulsers modifies delay amounts for driving signals in accordance with a transmission delay pattern set based on a sound velocity or a sound velocity distribution as selected according to a control signal from the controller 36 so that ultrasonic waves transmitted from the ultrasound transducers of the transducer array 42 form an ultrasonic beam, and supplies the driving signals to the ultrasound transducers.

The reception circuit 16 receives element data which is a reception signal each ultrasound transducer of the transducer array 42 outputs upon receipt of an ultrasonic echo from the subject, amplifies the element data associated with each ultrasound transducer, and supplies the element data which is analog to the A/D converter 20.

The A/D converter 20 converts the analog element data supplied from the reception circuit 16 into digital element data. The A/D converter 20 supplies the digital element data to a phasing adder 44 of the image generator 18 and also to the element data memory 22.

The image generator 18 produces a sound ray signal (reception data) from the digital element data supplied from the A/D converter 20 and generates an ultrasound image using the sound ray signal.

The image generator 18 includes the phasing adder 44, a signal processor 46, a digital scan converter (DSC) 48, an image processor 50 and an image memory 52.

Based on a receiving direction set by the controller 36, the phasing adder 44 selects one from among plural reception delay patterns set according to a sound velocity or a sound velocity distribution and stored in advance, applies a corresponding delay to each piece of element data in accordance with the selected reception delay pattern, and adds up the pieces of element data to thereby perform reception focusing processing. By this reception focusing processing, reception data (sound ray signal) is produced in which the ultrasonic echo is well focused.

The phasing adder 44 supplies the reception data to the signal processor 46.

The signal processor 46 corrects the reception data produced by the phasing adder 44 in terms of attenuation caused due to distance based on the depth at which the ultrasonic waves are reflected, and then performs envelope detection processing to thereby produce a B-mode image signal which is tomographic image information on a tissue inside the subject.

The DSC 48 converts the B-mode image signal produced by the signal processor 46 into an image signal compatible with an ordinary television signal scanning mode (raster conversion).

The image processor 50 performs various types of necessary image processing such as gradation processing on the B-mode image signal entered from the DSC 48 and then outputs the B-mode image signal to the display controller 32 or stores the B-mode image signal in the image memory 52.

The display controller 32 causes the monitor 34 to display an ultrasound image based on the B-mode image signal having undergone the image processing performed by the image processor 50.

The monitor 34 includes a display device such as an LCD, for example, and displays the ultrasound image under the control of the display controller 32.

The element data memory 22 sequentially stores the digital element data output from the A/D converter 20. The element data memory 22 also stores in association with the above element data information on a frame rate input by the controller 36. The information on a frame rate includes, for example, the depth at which an ultrasonic wave is reflected, the density of scanning lines, and a parameter representing the range of visual field.

The reconstructed image generator 24 calculates an optimal sound velocity at a region of interest to reconstruct an image of a region containing the region of interest under the control of the controller 36.

Figure 2:
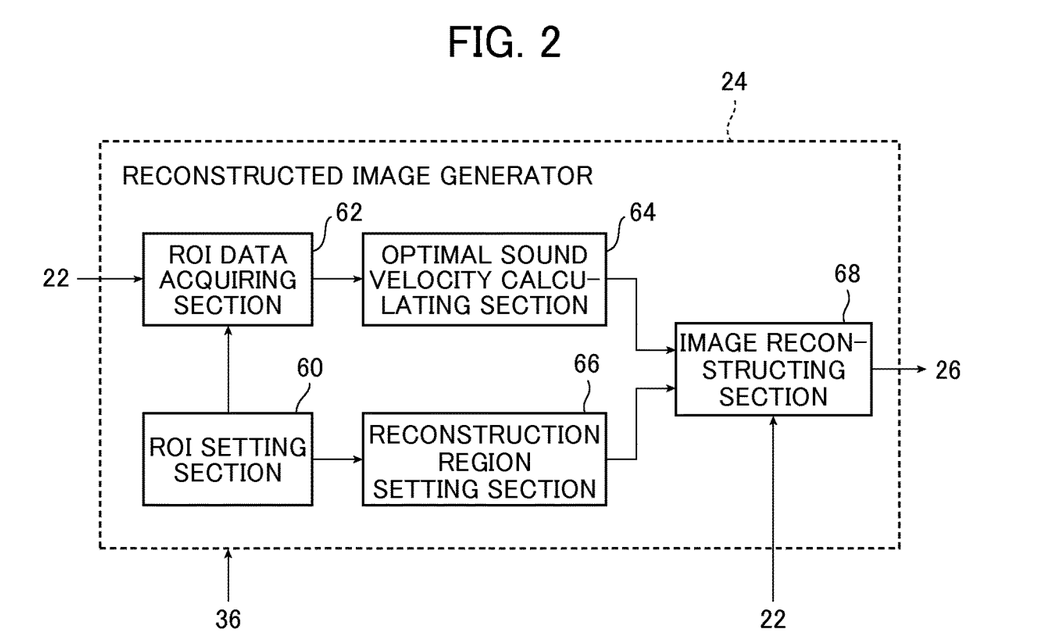
FIG. 2 is a block diagram conceptually showing the configuration of a reconstructed image generator shown in FIG. 1.

FIG. 2 is a block diagram conceptually showing the configuration of the reconstructed image generator 24.

As shown in FIG. 2, the reconstructed image generator 24 includes a region-of-interest (ROI) setting section 60, a ROI data acquiring section 62, an optimal sound velocity calculating section 64, a reconstruction region setting section 66 and an image reconstructing section 68.

The ROI setting section 60 sets a region of interest ROI in accordance with an input by the operator through the operating unit 38.

Figure 3:
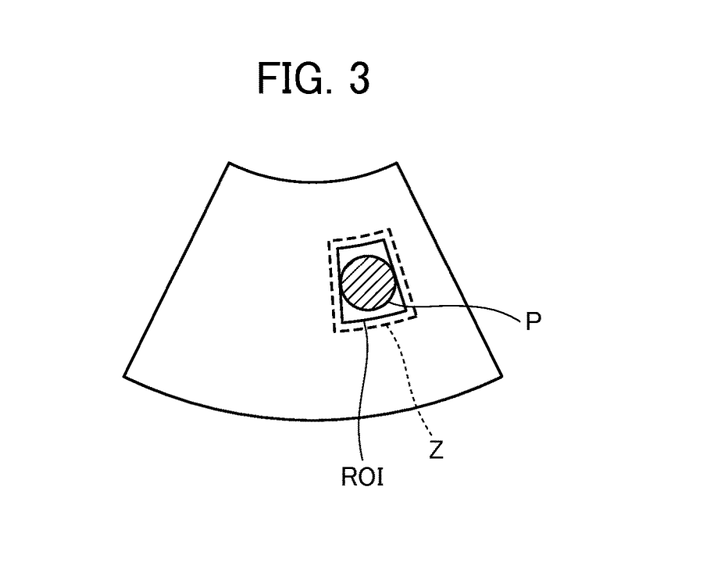
FIG. 3 is a diagram schematically showing a region of interest and reconstruction region as set.

FIG. 3 is a diagram schematically showing an example of an ultrasound image in which the region of interest ROI is set.

In the ultrasound image shown in FIG. 3, a target site P such as a tissue (organ) or lesion the operator desires to observe is captured, and the region of interest ROI is set so as to contain the target site P. Furthermore, a reconstruction region Z containing the region of interest ROI is set as indicated by dashed line in FIG. 3. The reconstruction region Z will be described later in detail.

The ROI setting section 60 supplies information on the set region of interest ROI to the ROI data acquiring section 62 and the reconstruction region setting section 66.

The ROI setting section 60 is not limited to the one configured to set a region of interest ROI in accordance with an input from the operating unit 38 but may set a region of interest ROI by analyzing an ultrasound image (B-mode image signal) generated by the image generator 18.

For instance, the ROI setting section 60 may extract a structural region based on the difference in brightness between adjacent pixels in an ultrasound image generated by the image generator 18. Specifically, the ROI setting section 60 may determine positions (pixels) where the difference in brightness between adjacent pixels is equal to or greater than a predetermined value as constituting the edge of a structural region (tissue or lesion), determine and extract a region surrounded by the edge or a region significantly containing the edge as the structural region, namely, an image of the target site P, and set a region containing the image of the target site P and having predetermined shape and size as the region of interest ROI.

When the region of interest ROI is set by analyzing an ultrasound image, the structural region may be identified as a single region. Alternatively, two or more portions different in continuity of the edge, brightness level or the like may be identified as regions which are determined and extracted as images of separate target sites P, and a region of interest ROI may be set for each of the target sites P.

The ROI data acquiring section 62 reads out element data for a position corresponding to the region of interest ROI from element data stored in the element data memory 22 based on the information on the region of interest ROI supplied from the ROI setting section 60 and supplies the element data as read out to the optimal sound velocity calculating section 64.

The ROI data acquiring section 62 is not limited to the one configured to read out element data for a position corresponding to the region of interest ROI from the element data memory 22. For instance, the configuration may be made in such a manner that after a region of interest ROI is set, the transducer array 42 transmits ultrasonic waves with a focus on a position corresponding to the set region of interest ROI. In this case, the ROI data acquiring section 62 acquires element data, which has been produced by transmitting ultrasonic waves to the position corresponding to the region of interest ROI and receiving the resulting ultrasonic echoes, as the element data for the position corresponding to the region of interest ROI.

The optimal sound velocity calculating section 64 calculates an optimal sound velocity at the set region of interest ROI.

The optimal sound velocity refers to a set sound velocity that allows an ultrasound image to have the highest contrast and/or sharpness when the set sound velocity is caused to vary in many ways and the reception focusing processing is performed based on various sound velocities to thereby generate ultrasound images. The optimal sound velocity may be determined based on, for example, image contrast or spatial frequency dispersion in a scanning direction as described in JP 08-317926 A.

For instance, the optimal sound velocity calculating section 64 causes a set sound velocity v to vary from 1400 m/s to 1650 m/s in increments of 50 m/s and calculates sharpness values of images of the region of interest ROI with respective set sound velocities v. More specifically, for each set sound velocity v, the optimal sound velocity calculating section 64 performs the reception focusing processing based on the relevant set sound velocity v and using the element data corresponding to the region of interest ROI that is supplied from the ROI data acquiring section 62, so as to produce a sound ray signal and form an ultrasound image from the sound ray signal, and calculates the sharpness of the image in the region of interest ROI for the relevant set sound velocity v.

The optimal sound velocity calculating section 64 compares the sharpness values of images generated with the respective set sound velocities v and defines the set sound velocity v allowing the highest sharpness as the optimal sound velocity.

The optimal sound velocity calculating section 64 supplies the calculated optimal sound velocity to the image reconstructing section 68.

The reconstruction region setting section 66 sets a region in which an image is reconstructed, i.e., a reconstruction region Z, using the optimal sound velocity calculated by the optimal sound velocity calculating section 64.

The reconstruction region setting section 66 defines a region that contains the region of interest ROI supplied from the ROI setting section 60 and that is larger than the region of interest ROI as the reconstruction region Z.

As an example, the reconstruction region setting section 66 sets the reconstruction region Z by adding a region having a predetermined width to the edge of the region of interest ROI as shown in FIG. 3. Hereinafter, a part of the reconstruction region Z other than the region of interest ROI is called "margin region."

The reconstruction region Z is not particularly limited in size but preferably has the margin region that is large enough to cover an area corresponding to movement of the probe or tissue. This enables the target site P to remain in the reconstruction region Z even when the target site P is displaced from the region of interest ROI due to movement of the probe or tissue.

The reconstruction region setting section 66 supplies information on the set reconstruction region Z to the image reconstructing section 68.

The image reconstructing section 68 reconstructs an image of the reconstruction region Z based on the optimal sound velocity.

The image reconstructing section 68 first reads out element data for a position corresponding to the reconstruction region Z from element data stored in the element data memory 22 based on the information on the reconstruction region Z supplied from the reconstruction region setting section 66. Next, the image reconstructing section 68 produces a sound ray signal by performing the reception focusing processing on the read element data based on the optimal sound velocity supplied from the optimal sound velocity calculating section 64 and produces a B-mode image signal for the reconstruction region Z from the sound ray signal. The image reconstructing section 68 then performs raster conversion as well as various necessary image processing such as gradation processing on the produced B-mode image signals to thereby generate a reconstructed image.

The image reconstructing section 68 supplies the generated reconstructed image to the image regenerator 26.

As described above, with the configuration in which in generating an ultrasound image, a region of interest is set in an ultrasound image and the optimal sound velocity at the region of interest is obtained, it is possible to improve the image quality at the region of interest, i.e., at a tissue or lesion the operator desires to observe, and obtain the optimal sound velocity value in a short time.

However, in the case where a region of interest is set in an ultrasound image, a tissue or lesion the operator desires to observe may be displaced from the set region of interest due to movement of the probe or tissue. When a region of interest is set and the optimal sound velocity value at the region of interest is obtained to thereby generate an ultrasound image, the ultrasound image is generated with the sound velocity value optimal for a tissue or lesion the operator desires to observe in the region of interest, whereas the ultrasound image is generated with a sound velocity value different from the sound velocity value optimal for the tissue or lesion the operator desires to observe in a region not within the region of interest. Accordingly, when the tissue or lesion the operator desires to observe is displaced from the region of interest, this may adversely affect the image quality.

To cope with it, the present invention reconstructs an image in a reconstruction region that contains a region of interest and is larger than the region of interest based on the optimal sound velocity at the region of interest. As a result, even when a tissue or lesion the operator desires to observe is displaced from the set region of interest, the resulting ultrasound image can have excellent image quality at the tissue or lesion the operator desires to observe.

The image regenerator 26 synthesizes the original ultrasound image with the reconstructed image supplied from the image reconstructing section 68 to regenerate an ultrasound image.

Specifically, the image regenerator 26 reads out an ultrasound image stored in the image memory 52 while acquiring the reconstructed image supplied from the image reconstructing section 68, replaces the reconstruction region Z of the ultrasound image by the reconstructed image to thereby generate a new ultrasound image.

The image regenerator 26 supplies the generated new ultrasound image to the display controller 32.

The image regenerator 26 is not limited to the forgoing configuration in which the image of the reconstruction region Z of the ultrasound image is replaced by the reconstructed image.

For instance, the image regenerator 26 may generate a new ultrasound image by combining a brightness value of each pixel of the image in the reconstruction region Z in the original ultrasound image and a brightness value of the corresponding pixel of the reconstructed image at a predetermined ratio to thereby obtain brightness values of respective pixels, and defining the resulting image as the image in the reconstruction region Z.

Alternatively, the image regenerator 26 may generate a new ultrasound image by replacing the image in the region of interest ROI by the corresponding part of the reconstructed image and replacing the image in the margin region by an image obtained by synthesizing the original ultrasound image in the margin region and the corresponding part of the reconstructed image. Still alternatively, the image in the margin region may be regenerated by synthesizing the original ultrasound image and the reconstructed image so that the reconstructed image makes up a greater proportion at a side closer to the region of interest and the proportion of the original ultrasound image increases with increasing distance from the region of interest.

The controller 36 controls the components in the ultrasound diagnostic apparatus 10 in accordance with an instruction entered by the operator through the operating unit 38.

When the operator enters an input for setting a region of interest ROI through the operating unit 38, the controller 36 supplies to the ROI setting section 60 information on the region of interest ROI as input through the operating unit 38.

The operating unit 38 is provided for the operator to perform input operations and may be composed of, for example, a keyboard, a mouse, a track ball, and/or a touch panel.

The operating unit 38 also includes an input device to be used by the operator to input information on the region of interest ROI.

The storage 40 stores, for example, an operation program and may be constituted by a recording medium such as a hard disk, a flexible disk, an MO, an MT, a RAM, a CD-ROM, or a DVD-ROM.

The phasing adder 44, the signal processor 46, the DSC 48, the image processor 50, the display controller 32 and the reconstructed image generator 24 are constituted by a CPU and operation programs for causing the CPU to perform various kinds of processing, but they may be each constituted by a digital circuitry.

While in this embodiment, the image reconstructing section 68 generating a reconstructed image and the image generator 18 generating an ultrasound image are provided separately, the present invention is not limited thereto and the image generator 18 may double as the image reconstructing section.

To be more specific, the configuration may be made so that after the optimal sound velocity calculating section 64 calculates the optimal sound velocity at the region of interest ROI and the reconstruction region setting section 66 sets the reconstruction region Z, in the image generator 18, the phasing adder 44 reads out element data corresponding to the reconstruction region Z and performs the reception focusing processing based on the optimal sound velocity at the region of interest ROI to thereby produce a sound ray signal; the signal processor 46 produces a B-mode image signal from the sound ray signal; the DSC 48 performs raster conversion on the B-mode image signal; and the image processor 50 performs the image processing to generate the reconstructed image.

Figure 4:
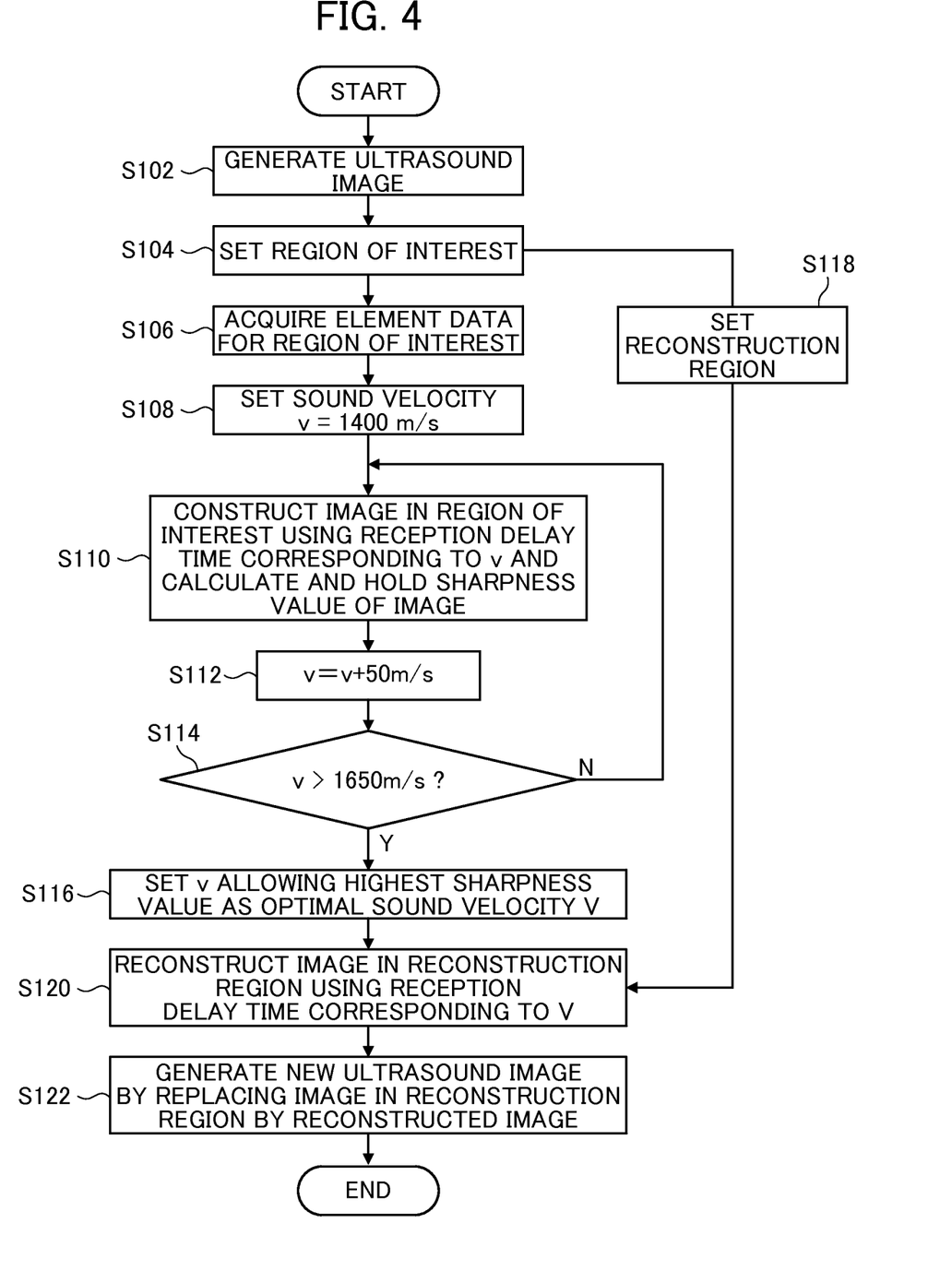
FIG. 4 is a flowchart for explaining the operation of the ultrasound image diagnostic apparatus shown in FIG. 1.

Next, the operation of the ultrasound diagnostic apparatus 10 is described more specifically with reference to a flowchart of FIG. 4.

When the operator holds the ultrasound probe 12 in contact with a surface of the subject and starts measurement, the transducer array 42 transmits ultrasonic beams in accordance with driving signals supplied from the transmission circuit 14, receives ultrasonic echoes from the subject and outputs reception signals (element data).

The reception circuit 16 amplifies the analog element data and supplies the amplified analog element data to the A/D converter 20. The A/D converter 20 converts the received analog element data into digital element data and supplies the digital element data to the phasing adder 44 of the image generator 18 and also to the element data memory 22.

The phasing adder 44 of the image generator 18 performs the reception focusing processing on the element data to produce reception data (sound ray signal) and supplies the reception data to the signal processor 46. The signal processor 46 processes the sound ray signal to produce a B-mode image signal. The DSC 48 performs raster conversion on the B-mode image signal, and the image processor 50 performs the image processing on the converted B-mode image signal to thereby generate an ultrasound image. The generated ultrasound image is stored in the image memory 52 and also displayed on the monitor 34 under the control of the display controller 32 (S102).

Next, the operator operates the operating unit 38 as referring to the displayed ultrasound image to input an instruction for setting a region of interest ROI. The ROI setting section 60 sets the region of interest ROI in accordance with the instruction input from the operating unit 38 (S104).

Once the region of interest ROI is set, the ROI data acquiring section 62 reads out element data for a position corresponding to the set region of interest ROI from the element data memory 22 based on the information on the region of interest ROI and supplies the element data to the optimal sound velocity calculating section 64 (S106).

The optimal sound velocity calculating section 64 causes a set sound velocity v to vary from 1400 m/s to 1650 m/s in increments of 50 m/s, performs the reception focusing processing based on the relevant set sound velocity v and using the element data for the position corresponding to the region of interest ROI, so as to produce a sound ray signal and form an ultrasound image from the sound ray signal, and calculates the sharpness of the image in the region of interest ROI for the relevant set sound velocity v (S108 to S114).

The optimal sound velocity calculating section 64 compares sharpness values of images formed with the respective set sound velocities v and defines the set sound velocity v allowing the highest sharpness as the optimal sound velocity V (S116).

On the other hand, the reconstruction region setting section 66 sets a reconstruction region Z by adding a margin region having a predetermined width to the edge of the set region of interest ROI (S118).

The image reconstructing section 68 reads out the element data for the position corresponding to the reconstruction region Z and performs the reception focusing processing based on the optimal sound velocity V so as to produce a sound ray signal and generate an image in the reconstruction region Z (reconstructed image) from the sound ray signal (S120).

The image regenerator 26 reads out the ultrasound image from the image memory 52, replaces the reconstruction region Z of the ultrasound image by the reconstructed image to thereby generate a new ultrasound image (S122).

Thus, the ultrasound diagnostic apparatus 10 of the invention calculates the optimal sound velocity at the set region of interest ROI and reconstructs the image in the reconstruction region Z covering a broader area than the region of interest ROI. As a result, even when a tissue or lesion the operator desires to observe is displaced from the set region of interest due to movement of the probe or tissue, the resulting ultrasound image can have excellent image quality at the tissue or lesion the operator desires to observe.

The present invention is basically as described above.

While the present invention has been described in detail above, the invention is not limited to the above embodiment and various modifications and improvements may be made without departing from the spirit of the invention.

What is claimed is:

1. An ultrasound image diagnostic apparatus, comprising:
   a transducer array having a plurality of oscillators and adapted to transmit an ultrasonic wave toward a subject, receive an ultrasonic echo from the subject and output element data which is a reception signal of each of the plurality of oscillators;
   an element data memory adapted to store the element data that each of the plurality of oscillators of the transducer array has output upon receipt of the ultrasonic echo; and
   a processor configured to:
   generate a first ultrasound image based on a sound ray signal produced from the element data output by the transducer array,
   acquire element data corresponding to a region of interest set in advance,
   calculate an optimal sound velocity at the region of interest using the element data corresponding to the region of interest as acquired,
   set a reconstruction region by adding a margin region having a preset width to the region of interest in a frame in which the region of interest is set,
   acquire element data corresponding to the reconstruction region from the element data stored in the element data memory, and generate a reconstructed image by reconstructing the first ultrasound image in the reconstruction region using the element data corresponding to the reconstruction region based on the calculated optimal sound velocity at the region of interest, the margin region of the reconstructed region being reconstructed based on the calculated optimal sound velocity at the region of interest, regenerate a second ultrasound image using the first ultrasound image generated and the reconstructed image generated, and wherein the processor regenerates the second ultrasound image by replacing the reconstruction region of the first ultrasound image by the reconstructed image.

2. The ultrasound image diagnostic apparatus according to claim 1, wherein the processor acquires the element data corresponding to the region of interest from the element data stored in the element data memory.

3. The ultrasound image diagnostic apparatus according to claim 1, wherein the processor acquires the element data that the transducer array has output upon transmission of an ultrasonic wave toward the region of interest and receipt of an ultrasonic echo.

4. An ultrasound image diagnostic apparatus, comprising:
a transducer array having a plurality of oscillators and adapted to transmit an ultrasonic wave toward a subject, receive an ultrasonic echo from the subject and output element data which is a reception signal of each of the plurality of oscillators;
an element data memory adapted to store the element data that each of the plurality of oscillators of the transducer array has output upon receipt of the ultrasonic echo; and
a processor configured to:
generate a first ultrasound image based on a sound ray signal produced from the element data output by the transducer array,
acquire element data corresponding to a region of interest set in advance,
calculate an optimal sound velocity at the region of interest using the element data corresponding to the region of interest as acquired,
set a reconstruction region by adding a margin region having a preset width to the region of interest in a frame in which the region of interest is set,
acquire element data corresponding to the reconstruction region from the element data in the element data memory, and generate a reconstructed image by reconstructing the first ultrasound image in the reconstruction region using the element data corresponding to the reconstruction region based on the calculated optimal sound velocity at the region of interest, the margin region of the reconstructed region being reconstructed based on the calculated optimal sound velocity at the region of interest, regenerate a second ultrasound image using the first ultrasound image generated and the reconstructed image generated, wherein the processor regenerates the second ultrasound image by replacing the reconstruction region of the first ultrasound image by an image obtained by synthesizing the first ultrasound image in the reconstruction region and the reconstructed image.

5. An ultrasound image diagnostic apparatus, comprising:
a transducer array having a plurality of oscillators and adapted to transmit an ultrasonic wave toward a subject, receive an ultrasonic echo from the subject and output element data which is a reception signal of each of the plurality of oscillators;
an element data memory adapted to store the element data that each of the plurality of oscillators of the transducer array has output upon receipt of the ultrasonic echo; and
a processor configured to:
generate a first ultrasound image based on a sound ray signal produced from the element data output by the transducer array,
acquire element data corresponding to a region of interest set in advance,
calculate an optimal sound velocity at the region of interest using the element data corresponding to the region of interest as acquired,
set a reconstruction region by adding a margin region having a preset width to the region of interest in a frame in which the region of interest is set,
acquire element data corresponding to the reconstruction region from the element data in the element data memory, and generate a reconstructed image by reconstructing the first ultrasound image in the reconstruction region using the element data corresponding to the reconstruction region based on the calculated optimal sound velocity at the region of interest, the margin region of the reconstructed region being reconstructed based on the calculated optimal sound velocity at the region of interest, regenerate a second ultrasound image using the first ultrasound image generated and the reconstructed image generated, wherein the processor regenerates the second ultrasound image by replacing the region of interest of the first ultrasound image by the reconstructed image in the region of interest and replacing the margin region of the first ultrasound image by an image obtained by synthesizing the first ultrasound image in the margin region and the reconstructed image in the margin region at a ratio varied such that a proportion of the first ultrasound image increases with increasing distance from the region of interest.

* * * * *